United States Patent [19]
Fisher

[11] Patent Number: 6,159,751
[45] Date of Patent: Dec. 12, 2000

[54] DEVELOPMENT OF DNA PROBES AND IMMUNOLOGICAL REAGENTS OF HUMAN TUMOR ASSOCIATED ANTIGENS

[75] Inventor: Paul B. Fisher, Scarsdale, N.Y.

[73] Assignee: The Trustees of Columbia University in the City of New York, New York, N.Y.

[21] Appl. No.: 08/463,699

[22] Filed: Jun. 5, 1995

Related U.S. Application Data

[62] Division of application No. 08/351,888, Dec. 8, 1994, which is a continuation of application No. 08/225,493, Apr. 11, 1994, abandoned, which is a continuation of application No. 08/106,323, Aug. 13, 1993, abandoned, which is a continuation of application No. 07/603,804, Oct. 25, 1990, abandoned.

[51] Int. Cl.[7] .............................. C12N 5/12; C12N 5/18; C12N 15/08; G01N 33/53
[52] U.S. Cl. ............... 436/548; 435/70.21; 435/70.1; 435/325; 435/330; 435/344; 435/440; 435/452; 435/455; 435/465; 435/354; 530/387.7; 530/388.8; 530/388.85; 530/808; 530/809
[58] Field of Search .................... 435/70.21, 172.1, 435/172.2, 240.1, 240.27, 70.1, 325, 330, 344, 440, 452, 455, 465, 354; 436/548; 530/387.7, 388.8, 388.85, 808, 809; 935/52, 70, 89, 102, 104

[56] References Cited

U.S. PATENT DOCUMENTS

| | | |
|---|---|---|
| 4,631,259 | 12/1986 | Clewell et al. . |
| 4,634,665 | 1/1987 | Axel et al. . |
| 4,681,840 | 7/1987 | Stephenson et al. . |
| 4,699,877 | 10/1987 | Cline et al. . |
| 4,786,718 | 11/1988 | Weinberg et al. . |
| 4,871,838 | 10/1989 | Bos et al. . |
| 4,892,935 | 1/1990 | Yoshida et al. . |
| 4,914,021 | 4/1990 | Toth et al. . |
| 4,935,341 | 6/1990 | Bargmann et al. . |
| 4,994,558 | 2/1991 | Armour et al. . |
| 4,996,298 | 2/1991 | Salem et al. . |
| 5,028,420 | 7/1991 | Masegi . |
| 5,283,058 | 2/1994 | Faustman . |

FOREIGN PATENT DOCUMENTS 0346702  12/1989  European Pat. Off. .

OTHER PUBLICATIONS

Drebin, J.A., et al. Monoclonal Antibodies Identify a Cell–Surface Antigen Associated with an Activated Cellular Oncogene, Nature 312:545–548 (1984).

Hollingsworth, M.A., et al., Antigens Expressed on NIH 3T3 Cells Following Transformation with DNA from a Human Pancreatic Tumor, Cancer Res. 46:2482–2487 (1986).

Liaw, W.–S., et al., Transfer of a Malignant Phenotype by Calcium–medicated DNA Transfection from Human Prostatic Carcinoma Cells to a Cloned Rat Embryo Fibroblast (CREF) Cell Line, J. Virol. 137:113A, Abstract 38 (1987).

Su, Z.–Z., et al., Transfer of a Dominant–Acting Tumor–Inducing Oncogene from Human Prostatic Carcinoma Cells to Cloned Rat Embryo Fibroblast Cells by DNA–Transfection, Anticancer Res. 12(2):297–304 (1992).

Shen et al., J. Nat. Cancer Inst., 86:91–98, 1994.

*Primary Examiner*—Ronald B. Schwadron
*Attorney, Agent, or Firm*—John P. White; Cooper & Dunham LLP

[57] ABSTRACT

This invention provides a method for preparing a hybridoma cell line which produces a monoclonal antibody which specifically recognizes and binds to a tumor associated antigen which comprises: (a) cotransfecting a CREF-Trans 6 cell line with DNA isolated from a neoplastic, human cell and a plasmid which encodes a selectable or identifiable trait; (b) selecting transfected cells which express the selectable or identifiable trait; (c) recovering the cells so selected in step (b); (d) injecting the cells so recovered in step (c) into a suitable marine host; (e) maintaining the resulting first murine host for a period of time effective to induce the cells injected in step (d) to form a tumor in the murine host; (f) isolating the tumor formed in step (e); (g) obtaining tumor cells from the isolated tumor in step (f); (h) coating the tumor cells obtained in step (9) with an antiserum generated against the CREF Trans-6 cell line (i) injecting the antiserum-coated cells from step (h) into a plurality of suitable second murine hosts; (j) screening the resulting second hosts from step (i) to identify hosts which produce serum reactive with the neoplastic human cell; (k) removing spleens from the second hosts so identified in step (j); (l) preparing from the spleens so removed in step (k) hybridomas; and (m) recovering therefrom a hybridoma cell line which produces a monoclonal antibody which specifically recognizes and binds to the tumor associated antigen.

4 Claims, 6 Drawing Sheets

DEVELOPMENT OF DNA PROBES AND IMMUNOLOGICAL REAGENTS OF HUMAN TUMOR ASSOCIATED ANTIGENS

This is a divisional application of Ser. No. 08/351,888, filed Dec. 8, 1994, which is a continuation of U.S. Ser. No. 08/225,493, filed Apr. 11, 1994, now abandoned, which is a continuation of U.S. Ser. No. 08/106,323, filed Aug. 13, 1993, now abandoned, which is a continuation of U.S. Ser. No. 07/603,804, filed Oct. 25, 1990, now abandoned.

Throughout this application, various publications are referenced by Arabic numerals within parentheses. Full citations for these publications may be found at the end of the specification immediately preceding the claims. The disclosures of these publications in their entirety are hereby incorporated by reference into this application in order to more fully describe the state of the art as known to those skilled therein as of the date of the invention described and claimed herein.

BACKGROUND OF THE INVENTION

A procedure which has proven successful in identifying dominant acting oncogenes associated with various human malignancies has been DNA transfection (1–3). By employing DNA $Ca^{2+}$-mediated DNA transfection techniques and various molecular cloning strategies, the genetic elements presumably responsible for malignant conversion of specific human and rodent cells have been identified and cloned (4–21). The primary method used to identify transforming oncogenes has been by $Ca^{2+}$-mediated DNA transfer of sheared HMW-tumor DNA into NIH-3T3 cells followed by the isolation and characterization of DNA from morphologically transformed foci. A limitation of this assay has been that the majority of HMW-DNA from primary and established human tumor isolates, approximately 80%, fail to induce morphological transformation of NIH-3T3 cells.

By using a modification of this procedure, the $Ca^{2+}$-mediated transfer of HMW-DNA plus the neomycin resistance gene into NIH-3T3 cells, selection for neomycin resistant colonies in G418-supplemented medium, injection of pooled neomycin resistant cells into nude mice and the generation and subsequent isolation of tumor cells, it has been possible to identify transforming DNA which either fails to form morphologically transformed foci or is weakly focus-producing when transfected into NIH-3T3 cells (1,12, 13).

More recent studies indicate that a specific clone of Fisher rat embryo cells, CREF (14), develops a tumorigenic phenotype in nude mice after being cotransfected with HMW-prostatic carcinoma DNA or HMW-colon carcinoma DNA in combination with pSV2-Neo plasmid DNA followed by selection for G418 resistant colonies (2). In contrast, both types of HMW-DNAs did not induce foci of morphologically altered CREF cells when assayed using a monolayer culture system (2). In addition, when the same HMW tumor-DNA samples and transfection protocol used with CREF cells were applied to NIH-3T3 cells, no tumors were induced by transfected cells in nude mice (2).

The recent development of hybridoma technology has resulted in the development of specific monoclonal antibodies to various human tumor associated antigens. This approach has greatly facilitated the study of the potential role of tumor associated antigens in expression of the neoplastic state (38). However, the production of monoclonal antibodies with good tumor specificity, especially toward various stages in the development of a malignant neoplasm, remains a laborious and uncertain undertaking, especially when freshly isolated heterogeneous tumor cells are used as immunogens. An innovative recent approach to the generation of monoclonal antibodies with specificity to transforming gene products which may be mediators of the tumor state, has been to utilize transfected heterologous species cells containing and expressing human transforming gene products as immunogens (39–42). Using this approach, monoclonal antibodies have been produced against the MM transforming gene transferred and expressed in NIH-3T3 cells. Similarly, Roth, et al. have used the transfection approach in generating monoclonal antibodies against NIH-3T3 transfectants produced following transfer of HMW-DNA from a human acute lymphocytic leukemia cell line (ALL) and to a c-Ha-ras transformed cell line (40, 41). In addition, Hollingsworth, et al. transfected NIH-3T3 cells with HMW-DNA from a human pancreatic adenocarcinoma cell line to generate monoclonal antibodies (42).

SUMMARY OF THE INVENTION

The present invention provides a general method for identifying genes and producing immunological reagents which encode cell surface antigens of human origin.

Specifically, this invention provides a method for preparing a hybridoma cell line which produces an antibody which specifically recognizes and binds to a cell surface antigen associated with a neoplastic, human cell. The method comprises: (a) cotransfecting an established non-human, non-tumorigenic cell line with DNA isolated from a neoplastic, human cell and DNA encoding a selectable or identifiable trait; (b) selecting transfected cells which express the selectable or identifiable trait; (c) recovering the transfected cells so selected; (d) injecting the transfected cells so recovered into a suitable first murine host; (e) maintaining the resulting first murine host for a period of time effective to induce the injected transfected cells to form a tumor in the first murine host; (f) isolating the resulting tumor from the first murine host; (g) obtaining tumor cells from the tumor so isolated; (h) coating the tumor cells so obtained with an antiserum generated against the established non-human, non-tumorigenic cell line; (i) injecting the antiserum-coated cells into suitable second hosts; (j) screening the resulting second hosts to identify hosts which produce serum reactive with the neoplastic, human cell; (k) removing spleens from the second hosts so identified; (l) preparing from the spleens so removed hybridomas; and (m) recovering therefrom a hybridoma cell line which produces an antibody which specifically recognizes and binds to the cell surface antigen.

This invention also provides a method for producing a monoclonal antibody which specifically recognizes and binds to a cell surface antigen associated with a neoplastic, human cell. This method comprises producing a hybridoma according to the above method and recovering from the hybridoma so produced the monoclonal antibody.

This invention further provides a method for preparing a polyclonal antibody which specifically recognizes and binds to a cell surface antigen associated with a neoplastic, human cell. This method comprises: (a) cotransfecting an established non-human, non-tumorigenic cell line with DNA isolated from a neoplastic, human cell and DNA encoding a selectable or identifiable trait; (b) selecting transfected cells which express the selectable or identifiable trait; (c) recovering the transfected cells so selected; (d) injecting the transfected cells so recovered into a suitable first murine host; (e) maintaining the resulting first murine host for a period of time effective to induce the injected transfected cells to form a tumor in the first murine host; (f) isolating the resulting tumor from the first murine host; (g) obtaining tumor cells from the tumor so isolated; (h) coating the tumor cells so obtained with an antiserum generated against the established non-human, non-tumorigenic cell line; (i) injecting the antiserum-coated cells into suitable second hosts; (j) screening the resulting second hosts to identify hosts which produce serum reactive with the neoplastic, human cell; and (k) recovering from the second hosts so identified the polyclonal antibody.

This invention provides a method of diagnosing in a subject a neoplastic condition which comprises contacting a sample from the subject with a monoclonal antibody labeled with a detectable marker under conditions permitting the antibody to specifically recognize and bind to the cell surface antigen associated with the neoplastic condition, detecting the presence of antibody bound to the antigen, and thereby diagnosing the neoplastic condition.

This invention also provides a method of diagnosing in a subject a neoplastic condition which comprises contacting a sample from the subject with a polyclonal antibody labeled with a detectable marker under conditions permitting the antibody to specifically recognize and bind to the cell surface antigen associated with the neoplastic condition, detecting the presence of antibody bound to the antigen, and thereby diagnosing the neoplastic condition.

This invention further provides a method of treating a neoplastic condition which comprises contacting neoplastic, human cells associated with the neoplastic condition with a monoclonal antibody labeled with a therapeutic agent under conditions such that, the therapeutic agent selectively inhibits proliferation of the neoplastic, human cells.

This invention also provides a method of treating a neoplastic condition which comprises contacting neoplastic, human cells associated with the neoplastic condition with a polyclonal antibody labeled with a therapeutic agent under conditions such that the therapeutic agent selectively inhibits proliferation of the neoplastic, human cells.

This invention provides a method of imaging a neoplastic, human cell which comprises contacting the neoplastic, human cell to be imaged with a monoclonal antibody labeled with an imaging agent under conditions permitting the antibody to specifically recognize and bind to the cell surface antigen associated with the neoplastic cell and detecting the imaging agent bound thereto, thereby imaging the neoplastic cell.

This invention also provides a method of imaging a neoplastic, human cell which comprises contacting the neoplastic, human cell to be imaged with a polyclonal antibody labeled with an imaging agent under conditions permitting the antibody to specifically recognize and bind to the cell surface antigen associated with the neoplastic cell and detecting the imaging agent bound thereto, thereby imaging the neoplastic cell.

This invention provides a method for preparing DNA encoding a cell surface antigen associated with a neoplastic, human cell. This method comprises: (a) cotransfecting CREF-Trans 6 cell line with DNA isolated from a neoplastic, human cell and DNA encoding a selectable or identifiable trait; (b) selecting transfected cells which express the selectable or identifiable trait; (c) recovering the transfected cells so selected; (d) injecting the transfected cells so recovered into a suitable first murine host; (e) maintaining the resulting first murine host for a period of time effective to induce the injected transfected cells to form a tumor in the first murine host; (f) isolating the resulting tumor from the first murine host; (g) obtaining tumor cells from the tumor so isolated; and (h) recovering DNA encoding the cell surface antigen associated with the neoplastic, human cell from the tumor cells so obtained.

This invention also provides a method of diagnosing in a subject a neoplastic condition which comprises contacting a sample from the subject with the DNA probe labeled with a detectable marker under conditions permitting the DNA probe to hybridize with the DNA associated with the neoplastic condition, detecting the presence of hybridized DNA, and thereby diagnosing the neoplastic condition.

DETAILED DESCRIPTION OF THE INVENTION

Figure 1:
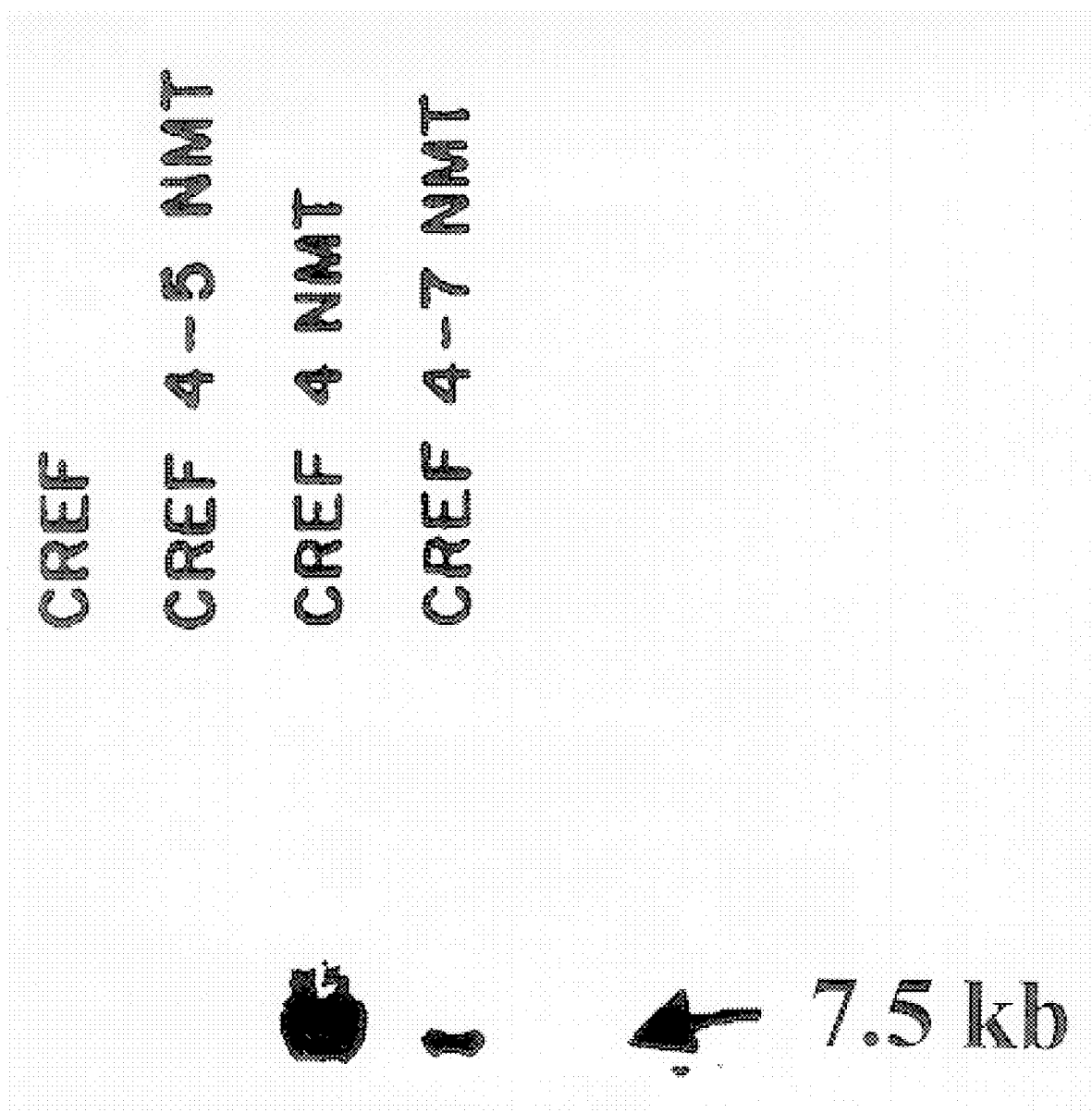
FIG. 1. Southern blot analysis. High molecular weight DNA from CREF-Trans 6 (represented as CREF in FIG. 1), a primary tumor obtained in nude mice following the injection of CREF-Trans 6 cells transfected with pSV2-neo and LNCap DNA (CREF-4 NMT) and two independent secondary tumors obtained following the injection into nude mice of CREF-Trans 6 cells with pSV2-neo and CREF 4 NMT DNA. Southern blots were probed with a 32P-labeled nick-translanted 300 bp Alu probe.

The present invention provides a general method for identifying genes and producing immunological reagents which encode cell surface antigens of human origin.

Specifically, this invention provides a method for preparing a hybridoma cell line which produces an antibody which specifically recognizes and binds to a cell surface antigen associated with a neoplastic, human cell. The method comprises: (a) cotransfecting an established non-human, non-tumorigenic cell line with DNA isolated from a neoplastic, human cell and DNA encoding a selectable or identifiable trait; (b) selecting transfected cells which express the selectable or identifiable trait; (c) recovering the transfected cells so selected; (d) injecting the transfected cells so recovered into a suitable first murine host; (e) maintaining the resulting first murine host for a period of time effective to induce the injected transfected cells to form a tumor in the first murine host; (f) isolating the resulting tumor from the first murine host; (g) obtaining tumor cells from the tumor so isolated; (h) coating the tumor cells so obtained with an antiserum generated against the established non-human, non-tumorigenic cell line; (i) injecting the antiserum-coated cells into suitable second hosts; (j) screening the resulting second hosts to identify hosts which produce serum reactive with the neoplastic, human cell; (k) removing spleens from the second hosts so identified; (l) preparing from the spleens so removed hybridomas; and (m) recovering therefrom a hybridoma cell line which produces an antibody which specifically recognizes and binds to the cell surface antigen.

As used herein, the established non-human, non-tumorigenic cell line may be any established cell line that is non-human, displays a nontransformed and nontumorigenic phenotype, and can efficiently take up and integrate foreign DNA consisting of both linked and unlinked chains. In the preferred embodiment of the invention the established non-human, non-tumorigenic cell line is the CREF-Trans 6 cell line which has been deposited with the American Type Culture Collection in 10801 University Blvd. Manassas, Va., 20110-2209 U.S.A., under ATCC Accession No. CRL 10584, deposited Oct. 25, 1990 (CREF-Trans 6).

As used herein, the neoplastic, human cell may be any neoplastic, human cell that is benign or metastatic and may be derived from any neoplastic, human cell line or any primary tumor, even very small quantities of primary tumor. In one embodiment of the invention, the neoplastic, human cell is a human prostatic carcinoma cell derived from cell line LNCaP. In another embodiment of the invention, the neoplastic, human cell is a human breast carcinoma cell derived from cell line T47D. In another embodiment of the invention, the neoplastic, human cell is a human colorectal carcinoma cell derived from cell line SW480. In another embodiment of the invention, the neoplastic, human cell is a human glioblastoma multiform (stage IV astrocytoma) cell derived from cell line GBM-18. In yet another embodiment of the invention, the neoplastic, human cell is a human glioblastoma multiform (stage IV astrocytoma) cell derived from a primary tumor.

As used herein, the DNA encoding the selectable or identifiable trait may be any DNA encoding a selectable or identifiable trait. In one embodiment of the invention, the DNA encoding the selectable or identifiable trait is plasmid DNA encoding resistance to an antibiotic. In the preferred embodiment of the invention, the plasmid DNA comprises pSV2-Neo and the antibiotic is G418.

As used herein, the suitable second host can be a murine host or a non-human primate host.

For the purposes of this invention, the cell surface antigen that is associated with a neoplastic, human cell may be any cell surface antigen. The cell surface antigen may be, but is not limited to the following embodiments: a tumor associated antigen, a growth factor receptor, a viral-encoded surface-expressed antigen, an antigen encoded by an oncogene product, a surface epitope, a membrane protein which mediates classical or atypical multi-drug resistance, an antigen which mediates a tumorigenic phenotype, an antigen which mediates a metastatic phenotype, an antigen which suppresses a tumorigenic phenotype, an antigen which suppresses a metastatic phenotype, an antigen which is recognized by a specific immunological effector cell such as a T-cell, and an antigen that is recognized by a non-specific immunological effector cell such as a macrophage cell or a natural killer cell. In the preferred embodiment of the invention, the cell surface antigen is a tumor associated antigen.

As used herein, the hybridoma cell line can be recovered using methods known to those of ordinary skill in the art.

This invention also provides a hybridoma cell line produced according to the above method.

As used herein, steps (a) through (g) may be repeated to obtain additional tumor cells, i.e. secondary transfectants, tertiary transfectants, etc.

This invention further provides a method for producing a monoclonal antibody which specifically recognizes and binds to a cell surface antigen associated with a neoplastic, human cell. This method comprises producing a hybridoma according to the above method and recovering from the hybridoma so produced the monoclonal antibody.

For purposes of this invention, the monoclonal antibody cn be recovered by methods known to those of ordinary skill in the art.

This invention also provides a monoclonal antibody produced according to the above method.

This invention provides a method for preparing a polyclonal antibody which specifically recognizes and binds to a cell surface antigen associated with a neoplastic, human cell. This method comprises: (a) cotransfecting an established non-human, non-tumorigenic cell line with DNA isolated from a neoplastic, human cell and DNA encoding a selectable or identifiable trait; (b) selecting transfected cells which express the selectable or identifiable trait; (c) recovering the transfected cells so selected; (d) injecting the transfected cells so recovered into a suitable first murine host; (e) maintaining the resulting first murine host for a period of time effective to induce the injected transfected cells to form a tumor in the first murine host; (f) isolating the resulting tumor from the first murine host; (g) obtaining tumor cells from the tumor so isolated; (h) coating the tumor cells so obtained with an antiserum generated against the established non-human, non-tumorigenic cell line; (i) injecting the antiserum-coated cells into suitable second hosts; (j) screening the resulting second hosts to identify hosts which produce serum reactive with the neoplastic, human cell; and (k) recovering from the second hosts so identified the polyclonal antibody.

For purposes of this invention, the polyclonal antibody can be recovered by methods known to those of ordinary skill in the art.

As used herein, the established non-human, non-tumorigenic cell line may be any established cell line that is non-human, displays a nontransformed and nontumorigenic phenotype, and can efficiently take up and integrate foreign DNA consisting of both linked and unlinked chains. In the preferred embodiment of the invention the established non-human, non-tumorigenic cell line is the CREF-Trans 6 cell line (ATCC Accession No. CRL10584).

As used herein, the neoplastic, human cell may be any neoplastic, human cell that is benign or metastatic and can be derived from any neoplastic, human cell line or any primary tumor, even small quantities of primary tumor. In embodiment of the invention the neoplastic, human cell is a human prostatic carcinoma cell derived from cell line LNCaP. In another embodiment of the invention the neoplastic, human cell is a human breast carcinoma cell derived from cell line T47D. In another embodiment of the invention the neoplastic, human cell is a human colorectal carcinoma cell derived from cell line SW480. In another embodiment of the invention the neoplastic, human cell is a human glioblastoma multiform (stage IV astrocytoma) cell derived from cell line GBM-18. In yet another embodiment of the invention, the neoplastic, human cell is a human glioblastoma multiform (stage IV astrocytoma) cell derived from a primary tumor.

As used herein, the DNA encoding the selectable or identifiable trait can be any DNA encoding a selectable or identifiable trait. In one embodiment of the invention, the DNA encoding the selectable or identifiable trait is plasmid DNA encoding resistance to an antibiotic. In the preferred embodiment of the invention, the plasmid DNA comprises pSV2-Neo and the antibiotic is G418.

As used herein, the suitable second host can be a murine host or a non-human primate host.

For purposes of this invention, the cell surface antigen that is associated with a neoplastic, human cell may be any cell surface antigen. The cell surface antigen may be, but is not limited to the following embodiments: a tumor associated antigen, a growth factor receptor, a viral-encoded surface-expressed antigen, an antigen encoded by an oncogene product, a surface epitope, a membrane protein which mediates a classical or atypical multi-drug resistance, an antigen which mediates a tumorigenic phenotype, an antigen which mediates a metastatic phenotype, an antigen which suppresses a tumorigenic phenotype, an antigen which suppresses a metastatic phenotype, an antigen which is recognized by a specific immunological effector cell such as a T-cell, and an antigen that is recognized by a non-specific immunological effector cell such as a macrophage cell or a natural killer cell. In the preferred embodiment of the invention, the cell surface antigen is a tumor associated antigen.

As used herein, steps (a) through (g) may be repeated to obtain additional tumor cells, i.e. secondary tranfectants, tertiary transfectants, etc.

This invention also provides a polyclonal antibody produced according to the above method.

This invention provides a monoclonal antibody labeled with a detectable marker.

As used herein, the detectable markers are well known to those of ordinary skill in the art and may be, but are not limited to enzymes, paramagnetic ions, biotins, fluorophores, chromophores, heavy metals, or radioisotopes.

This invention also provides a method of diagnosing in a subject a neoplastic condition which comprises contacting a sample from the subject with a monoclonal antibody labeled with a detectable marker under conditions permitting the antibody to specifically recognize and bind to the cell surface antigen associated with the neoplastic condition, detecting the presence of antibody bound to the antigen, and thereby diagnosing the neoplastic condition.

This invention provides a polyconal antibody labeled with a detectable marker.

As used herein, the detectable markers are well known to those of ordinary skill in the art and may be, but are not limited to enzymes, paramagnetic ions, biotins, fluorophores, chromophores, heavy metals, or radioisotopes.

This invention also provides a method of diagnosing in a subject a neoplastic condition which comprises contacting a sample from the subject with a polyclonal antibody labeled with a detectable marker under conditions permitting the antibody to specifically recognize and bind to the cell surface antigen associated with the neoplastic condition, detecting the presence of antibody bound to the antigen, and thereby diagnosing the neoplastic condition.

This invention provides for a monoclonal antibody labeled with a therapeutic agent.

As used herein, the therapeutic agents are well known to those of ordinary skill in the art and may be, but are not limited to antibiotics, antiviral agents, such as interferon, toxins, radioisotopes, or chemotherapeutic agents.

This invention also provides a method of treating a neoplastic condition which comprises contacting neoplastic, human cells associated with the neoplastic condition with a monoclonal antibody labeled with a therapeutic agent under conditions such that the therapeutic agent selectively inhibits proliferation of the neoplastic, human cells.

This invention provides for a polyclonal antibody labeled with a therapeutic agent.

As used herein, the therapeutic agents are well known to those of ordinary skill in the art and may be, but are not limited to antibiotics, antiviral agents, such as interferon, toxins, radioisotopes, or chemotherapeutic agents.

This invention also provides a method of treating a neoplastic condition which comprises contacting neoplastic, human cells associated with the neoplastic condition with a polyclonal antibody labeled with a therapeutic agent under conditions such that the therapeutic agent selectively inhibits proliferation of the neoplastic, human cells.

This invention provides a monoclonal antibody labeled with an imaging agent.

As used herein, the imaging agents are well known to those or ordinary skill in the art and may be, but are not limited to radioisotopes, dyes or enzymes such as peroxidase or alkaline phosphate, paramagnetic ions, or elements opaque to x-rays.

This invention provides a,method of imaging a neoplastic, human cell which comprises contacting the neoplastic, human cell to be imaged with a monoclonal antibody labeled with an imaging agent under conditions permitting the antibody to specifically recognize and bind to the cell surface antigen associated with the neoplastic cell and detecting the imaging agent bound thereto, thereby imaging the neoplastic cell.

As used herein, the method of imaging may comprise any of the numerous methods of imaging known to those of ordinary skill in the art such as, but not limited to visualizing radiation emitted by a radioactive isotope.

This invention provides a polyclonal antibody labeled with an imaging agent.

As used herein, the imaging agents are well known to those or ordinary skill in the art and may be, but are not limited to radioisotopes, dyes or enzymes such as peroxidase or alkaline phosphate, paramagnetic ions, or elements opaque to x-rays.

This invention also provides a method of imaging a neoplastic, human cell which comprises contacting the neoplastic, human cell to be imaged with a polyclonal antibody labeled with an imaging agent under conditions permitting the antibody to specifically recognize and bind to the cell surface antigen associated with the neoplastic cell and detecting the imaging agent bound thereto, thereby imaging the neoplastic cell.

As used herein, the method of imaging may comprise any of the numerous methods of imaging known to those of ordinary skill in the art such as, but not limited to visualizing radiation emitted by a radioactive isotope.

This invention provides a method for preparing DNA encoding a cell surface antigen associated with a neoplastic, human cell. This method comprises: (a) cotransfecting the CREF-Trans 6 cell line with DNA isolated from a neoplastic, human cell and DNA encoding a selectable or identifiable trait; (b) selecting transfected cells which express the selectable or identifiable trait; (c) recovering the transfected cells so selected; (d) injecting the transfected cells so recovered into a suitable first murine host; (e) maintaining the resulting first murine host for a period of time effective to induce the injected transfected cells to form a tumor in the first murine host; (f) isolating the resulting tumor from the first murine host; (g) obtaining tumor cells from the tumor so isolated; and (h) recovering DNA encoding the cell surface antigen associated with the neoplastic, human cell from the tumor cells so obtained.

As used herein, steps (a) through (g) may be repeated to obtain additional tumor cells, i.e. secondary transfectants, tertiary secondary etc.

This method for preparing DNA is an improvement over past methods because this aspect of the invention employs a new cloned rat embryo fibroblast cell line, specifically the CREF-Trans 6 cell line. The CREF-Trans 6 cell line permits the identification of genes mediating a tumor phenotype and cell surface antigen expression using small quantities of tumor tissue. The CREF-Trans 6 cell line also allows for easy detection of human repetitive sequences that serve as a genetic marker delineating the location of genes relevant to the induction of the tumor phenotype and cell surface expression. In addition, the expression of many known oncogenes have not been observed in tumor cells derived from the CREF cell line(21). This argues for the possibility of using this system to identify potentially new classes of human oncogenes.

As used herein, the method for recovering DNA from the tumor cells so obtained may comprise any of the numerous methods of isolating, purifying and cloning DNA known to one of ordinary skill in the art. This methods may be, but are not limited to polymerase chain reaction or classic phage cloning techniques.

As used herein the neoplastic, human cell may be any neoplastic, human cell that is benign or metastatic and can be derived from any neoplastic, human cell line or any primary tumor, even small quantities of primary tumor. In one embodiment of the invention the neoplastic, human cell is a human prostatic carcinoma cell derived from cell line LNCaP. In another embodiment of the invention the neoplastic, human cell is a human breast carcinoma cell derived from cell line T47D. In another embodiment of the invention the neoplastic, human cell is a human colorectal carcinoma cell derived from cell line SW480. In another embodiment of the invention the neoplastic, human cell is a human glioblastoma multiform (stage IV astrocytoma) cell derived from cell line GBM-18. In yet another embodiment of the invention, the neoplastic, human cell is a human glioblastoma multiform (stage IV astrocytoma) cell derived from a primary tumor.

As used herein the DNA encoding the selectable or identifiable trait may be any DNA encoding a selectable or identifiable trait. In one embodiment of the invention, the DNA encoding the selectable or identifiable trait is plasmid DNA encoding resistance to an antibiotic. In the preferred embodiment of the invention, the plasmid DNA comprises pSV2-Neo and the antibiotic is G418.

For purposes of this invention, the cell surface antigen that is associated with a neoplastic, human cell may be any cell surface antigen. The cell surface antigen may be, but is not limited to the following embodiments: a tumor associated antigen, a growth factor receptor, a viral-encoded surface-expressed antigen, an antigen encoded by an oncogene product, a surface epitope, a membrane protein which mediates classical or atypical multi-drug resistance, an antigen which mediates a tumorigenic phenotype, an antigen which mediates a metastatic phenotype, an antigen which suppresses a tumorigenic phenotype, an antigen which suppresses a metastatic phenotype, an antigen which is recognized by a specific immunological effector cell such as a T-cell, and an antigen that is recognized by a non-specific immunological effector cell such as a macrophage cell or a natural killer cell. In the preferred embodiment of the invention, the cell surface antigen is a tumor associated antigen.

This invention provides DNA prepared according to the above method.

This invention also provides a DNA probe hybridizable with the DNA above.

This invention further provides a DNA probe from above which is labeled with a detectable marker.

This invention also provides a method of diagnosing in a subject a neoplastic condition which comprises contacting a sample from the subject with the DNA probe labeled with a detectable marker under conditions permitting the DNA probe to hybridize with the DNA associated with the neoplastic condition, detecting the presence of hybridized DNA, and thereby diagnosing the neoplastic condition. The presence of the probe indicates the detection of a neoplastic condition.

The present invention is further illustrated in the Experimental Details section which follows. This section is set forth to aid in an understanding of the invention but is not intended to, and should not be construed to, limit in any way the invention as set forth in the claims which follow.

EXPERIMENTAL DETAILS

Materials and Methods

CREF-Trans 6 Coll Line.

The CREF-Trans 6 cell line is a subclone of the CREF cell line which is a specific clone of Fisher F2408 rat embryo cells (33). It was developed by plating CREF cells at low densities (50 and 100 cells/6-cm plate) and isolating a series of single-cell subclones.

These subclones of CREF (identified as CREF-Trans 1 through CREF-Trans 20) were then tested for their ability to be morphologically transformed following transfection with the Ha-ras (T24) oncogene. They were also analyzed for their ability to form antibiotic resistant colonies when transfected with a cloned neomycin resistance gene (pSV2neo) and selected for growth in medium containing G418. CREF-Trans 6 is a specific subclone of CREF which was found to be more sensitive than parental or other CREF-Trans subclones to transformation by T24 and for the development of neomycin resistance.

Other Coll Lines.

The LN-CaP cell line was derived from a human prostatic carcinoma. The T47D cell line was derived from a human breast carcinoma. The GBM-18 cell line was derived from a human glioblastoma multiform (stage IV astrocytoma). There was also a human glioblastoma multiform (stage IV multiform) derived from a primary tumor. The SW480 cell line was derived from a human colorectal carcinoma. The MCF-7 cell line was derived from a human blast carcinoma. The Colo38 cell line was derived from a human melanoma. The HO-I cell line was derived from a human melanoma. These cell lines are publicly available to those of ordinary skill in the art.

Preperation of Anti-Serum

BALB/c female mice (8 to 10 weeks old) were hyperimmunized with CREF-Trans 6 cells. They received: (l) one subcutaneous (sc) injection of scraped cells with complete Freund's adjuvant (1:1) on day 0; (2) one sc injection of scraped cells with incomplete Freund's adjuvant (1:1) on day 7; and (3) two intraperitoneal (ip) injections of scraped cells in Hanks' balanced salt solution on days 14 and 21. Mice were then bled from the retro-orbital eye socket and the pooled sera was tested for anti-CREF activity by ELISA. CREF cells were: (l) grown in 96-well microliter plates to near confluency; (2) the cells were fixed with 3.7% formal in PBS (5 min. at room temperature) and blocked with 10% normal goat serum; (3) antisera was tittered against the cells (serial dilutions; 2 hrs. at 37° C.); (4) binding was detected by using a goat anti-mouse lg secondary antibody conjugated to horseradish peroxidase (G X MIg-HRP; 60 min; 37° C.); and (5) a chromogen was added in the presence of $H_2O_2$ and a positive binding was reflected by a color change which was quantitated using a spectrophotometer. By employing the above procedures a high titer serum was obtained by day 21 (1:3200–1:6400) and used at a 1:100 for coating CREF-Trans 6 cells in initial experiments. A second high titer anti-serum (1:12400) was used in subsequent experiments.

Cotraisfection of the CREF-Trans 6 Coll Line

DNA transfections of recipient CREF cells have been performed as described previously (1, 3, 22), except the HMW-DNA has been sheared to produce DNA fragments of 6 to 25 kilobase pairs. This modification results in a more efficient transfer of certain cellular genes by calcium phosphate mediated DNA transfection and also tends to diminish the toxicity often encountered when transfecting HMW-DNA (111). DNA was then isolated from the cell lines using the phenol extraction method (14, 37). This HMW-DNA was then sheared by repeated passage through a syringe containing a 16-gauge needle and then sized by electrophoresis through agarose gels (36). The HMW-DNA was then be mixed with pSV2-Neo DNA (using a 20 to 40 $\mu$g: 1 $\mu$g ratio of HMW-DNA: Neo plasmid DNA) and 20 or 40 $\mu$g of final DNA was added as a calcium phosphate precipitate to 1 to $2\times10^6$ CREF-Trans cells (1, 3, 22). After incubation of CREF-Trans cells with the calcium phosphate-DNA precipitate for 4 hrs, the excess DNA-precipitate was removed, cultures were briefly treated with glycerol (15% glycerol: PBS col/vol) and cultures were resuspended by brief trypsin/versene treatment and replated at $5-10^4$, $10^5$ and $2.5-10^5$ cells/10 cm plate.

Selection of Transfected Expressing the Selectable or Identifiable Trait.

Forty-eight hrs post-plating, the medium will be replaced with medium containing G418 (500 $\mu$g/ml) (1,36). The selective medium was changed two times per week and colonies of NeoR should be detectable within 7 to 14 days.

Recovery and Injection of Transfected Cells in Mice.

After cell cultures from individual plates have been expanded to adequate numbers, the cells from each separate G418 selected plate were pooled and $10^6$ were injected subcutaneously per nude mouse.

Isolating and Obtaining the Tumor Cells.

If the injection of the transfected cells induces tumors in mice during an eight week incubation period, the tumors will be removed and reestablished in cell culture. The cells were removed from plates by either non-enzymatic dissociation or by scraping with a rubber policeman. Resuspended cells were washed with Hanks BSS and resuspended in a minimal volume of Hank's BSS.

Coating the Tumor Cells with Antiserum.

In order to block antigens normally expressed on CREF-Trans 6 cells from generating an immune response, tumor cells from the tumor were coated with high titer mouse anti-CREF-Trans 6 antisera prior to injection into mice. Resuspended cells (1 to $2.5\times10^6$ cells) were mixed with M X CREF anti-sera at a concentration of 1:100 (antisera:cells) and incubated for 4 to 6 hrs at room temperature or overnight at 4° C. on a shaker.

Injecting the Antiserum-coated Cells into Mice.

BALB/c female mice (8 to 10 weeks old) were then repeatedly injected ip with and without adjuvant over a month period, or longer with antisera-coated cells.

Screening of Hosts for Serum Reactive with Neoplastic Cell.

Pooled bleeds of mice immunized as described above were tested by ELISA for binding to various cells, including CREF-Trans 6, CREF 4-NMT (transfected with LNCaP DNA), LNCaP (human prostatic carcinoma cell line), SW480 (human colorectal carcinoma cell line), MCF-7 (human breast carcinoma cell line), HO-1 (human melanoma cell line), Colo 38 (human melanoma cell line), and human skin fibroblasts. Animals which were identified as having sera reactive with the appropriate human tumor cells were then used to generate MoAbs by standard procedures.

Generation of Monoclonal Antibodies.

The procedures we have utilized to generate MoAbs are similar to those described previously for generating MoAbs toward human TAAs (50), HLA antigens (51), type 5 adenovirus-transformed Sprague-Dawley rat embryo cells (52), X-ray-transformed C3H-10T 1/2 cells (53) and NIH-3T3 transfectants containing and expressing the neuro/glioblastoma (neu) oncogene (39). Spleen cells prepared from immunized mice were hybridized with the non-secreting myeloma cells NSI in the presence of polyethyleneglycol (PEG) according to the procedure of Kohler and Milstein (54) with minor modifications. Twenty-four hours after fusion the hybrid clones were replated in 96 well plates in HAT medium to select for hybrid cells.

The supernatant of microtiter wells containing expanded hybrid clones were then collected and tested for antibody activity against multiple target cells, including tertiary and secondary LN-CAP-CREF transfectants and normal CREF cells. For initial screening, a modification of the Terasaki plate $^{125}$I-protein A binding assay (55) were used because it requires a minimal number of target cells and the procedure is not time consuming. Other assay methods, e.g enzyme-linked immunoassay, are also available and will be employed if necessary. Following initial screening, the hybridoma culture supernatant which reacted specifically with the LN-CaP-CREF transfectants was retested for specificity against a larger panel of target cells which may include, the prostatic carcinoma cell lines DU-145, PC-3, two melanoma cell lines (Colo 38 and HO-1 cells) (69, 70, 139), a B lymphoblastoid cell line (WIL-2), normal human skin fibroblasts, and CREF-Trans 6 cells transformed by other agents (type 5 adenovirus, bovine papilloma virus type 1 and Ha-ras). The hybridomas that secrete antibody specific for the prostate tumor cell lines may be immediately subcloned at least 5 times by limiting dilution. The final hybridoma clones of interest, i.e. those which produce antibody which reacts specifically with human prostate cainoma TAAs, may expanded in vitro into mass cultures or in vivo as ascites in pristane primed syngeneic mice. Antibodies of interest will then be used to characterize biochemically the prostate tumor-inducing antigens expressed on transfected CREF cells and human prostatic carcinoma cells.
Generation of Polyclonal Antibodies.

Polyclonal antibodies were produced using procedures known to those of ordinary skill in the art from the animals identified as having sera reactive with the appropriate human tumor cells.

Identification of Specific Antigens using Antibodies.

MoAbs of interest will be used to isolate specific antigen (s) from human prostatic carcinoma cells for biochemical analysis using procedures described previously. Initially, simple experiments may be carried out to determine the nature of the molecules (i.e. protein or glycolipid) bearing the epitopes recognized by the MoAbs. To identify protein or glycoprotein antigens, a radioimmuniprecipitation assay (56, 57) will be used: Detergent extracts of cell,membranes from cells labeled with $^{125}$I or cells synthetically labeled with $^{35}$S-methionine or $^{3}$H-leucine will be reacted with MoAb bound to anti-mouse (IgG+IgM)-sepharose; and the MoAb-antigen interaction will be analyzed by SDS-PAGE (56, 57). To identify glycolipid antigens, the lipid components isolated from human prostatic carcinoma cells may first resolved be thin-layer chromatography and the chromatogram will then be reacted with the relevant MoAb.

The molecular weight and charge heterogeneity of the protein antigens will be further analyzed by two dimensional (2-D) gell electrophoresis as previously described by O'Farrell (58) and modified by Garrels (59). The antigens isolated by immunoprecipitation with MoAbs may then subjected to isoelectric focusing in the first dimension in polyacrylamide gels containing ampholines and urea. The gels may then be equilibrated with SDS-gel buffer and applied to an SDS-PAGE gel. The charge heterogeneity due to sialic acid will be assessed by removing these residues with neuraminidase prior to 2-D analysis. The 2-D analysis thus provides simultaneously the isoelectric point (pI) and the molecular weight of proteins being analyzed.

To determine the stability of the protein antigen recognized by the MoAb, Western blotting analysis may performed. Briefly, cellular extracts denatured by SDS detergent may be resolved by SDS-PAGE under reducing or non-reducing conditions, blotted onto nitrocellulose membranes and stained with selected MoAbs using the immunoperoxidase method (blot will be treated with MAb followed by a peroxidase conjugated anti-mouse Ig antibody followed by $H_2O_2$ plus 3, 3'-diaminobenzidine tetrahydrochloride) or the blotted antigen will be bound with purified MoAb followed by $^{125}$I-labeled *Staphylococcus aureus* protein A and autoradiography. These procedures will indicate: (a) whether the epitope remains immunoreactive following the treatment protocol; and (b) whether the protein antigen consists of subunits. Moreover, these studies will indicate whether the immunoblotting assay can be applied in the detection of the specific antigen(s) in patients' specimens.

Recovering DNA from the Tumor Cells.

Using the tumor cells derived from the tumors, DNA can be recovered, identified, isolated and molecularly cloned employing known procedures. Southern blot analyses will determine if human DNA sequences are present within DNA extracted from tumor-derived cell lines that are progeny of primary, secondary, or tertiary transfections of the CREF-Trans 6 cells. Usually there are high numbers of human DNA-containing fragments (Alu) in restriction endonuclease digested DNA from primary rat or mouse transfected cells, while the secondary and tertiary transfectants yield few Alu DNA-fragments, one or no bands on a Southern blot probed using human Alu DNA. In Southern blot analyses, we used the 265 bp Alu DNA sequence, Blur-8 (23), that has been subcloned into a vector containing an SP6 promoter (provided by V. Racaniello) in order to generate $^{32}$P-labeled probe RNA of high specific activity. Owing to the small size of the Blur-8 probe, it is possible not to detect single copy representations of the Alu repeat integrated within heterologous species DNA. To determine if Alu DNA sequences can be detected in transfected rat cells containing only a single copy of Alu DNA, DNA from a cell line provided by V. Racaniello, Columbia University, which has previously been shown to contain a single copy of Alu DNA, has been included as a hybridization control. If Southern blot analyses reveal the presence of conserved human Alu DNA containing restriction fragments in multiple secondary or tertiary transfectants, it should be possible to isolate the human prostatic carcinoma genes responsible for tumorigenic conversion of CREF cells. This will be accomplished by the generation of genomic DNA libraries, isolation of cloned DNA-containing Alu DNA sequences, and subsequently testing the biological activity of these cloned human DNAs by cotransfecting CREF cells with pSV2-Neo DNA and determining if G413-resistant transfectants are now tumorigenic in nude mice.

Partial MboI digests of DNA extracted from tumor-derived secondary or tertiary LN-CAP DNA transfected CREF cells may be used in the construction of lambda EMPL3 (BamHI site) libraries (26) and these libraries may be screened by plaque hybridization (27) using the Blur-8 Alu DNA probe. DNA may then be extracted from recombinant lambda phage that contain Alu sequences and cloned human DNA will be assayed for its tumor inducing ability by cotransfecting CREF cells with pSV2-Neo DNA and scoring the G418-resistant population for tumorigenic potential in nude mice after subcutaneous injection of $10^6$ cells. If a recombinant phage contains a tumor-inducing gene from LN-CAP prostatic carcinoma cells, the cloned DNA may be mapped using restriction endonucleases, and the smallest fragment of cloned DNA which retains the ability to transform CREF cells to an oncogenic phenotype will be used to determine, in LN-CAP and normal human prostate tissues: (a) the newly isolated gene transcription rate by nuclear run-off assay of the newly isolated gene; (b) the level and abundance of introns homologous poly $A^+$ RNA by Northern blot analysis; (c) the intron/exon arrangement using $S_1$ analysis (28); and, (d) using Southern blot analysis, if the DNA arrangement in the genome of normal human prostate cells. Comparison, by Southern analysis, of normal, LN-CaP and primary, secondary, and tertiary LN-CaP transfected CREF cells will also permit one to determine if there is amplification of the genes responsible for the oncogenic phenotype of these prostatic carcinoma cells.

If there are recombinant phage from the secondary or tertiary transfectants that contain Alu DNA, but do not transform CREF-6 cells to the tumorigenic state in nude mice, these recombinant phage will be used to screen cosmid (pJB8) (27) and lambda EMBL3 phage libraries constructed from LN-CAP DNA partially digested with MboI or EcoRI. DNA contained in phage or cosmids that hybridizes to the probe generated from the original transfectant DNA/lambda libraries may then be mapped extensively using restriction endonucleases and DNA within the phage or the cosmids that appears to contain homologous sequences, in addition to flanking DNA, may then be used to transfect CREF-Trans 6 cells followed by analysis of transfectants for tumorigenic potential in nude mice. Those cellular DNA sequences within phage or cosmids that generate transfectants scoring positive in the nude mouse tumorigenicity assay may then be digested with various restriction endonucleases to determine the smallest DNA sequence responsible for tumor-inducing activity.

If there are no human Alu DNA-containing sequences cloned within a single phage or cosmid constructed from the secondary or tertiary transfectants that can convert CREF cells to an oncogenic phenotype, one may attempt to complement the oncogene by supplying an overlapping fragment from a normal human or LN-CAP DNA lambda EMBL3 or cosmid library generated by partial digestion using either SalI or EcoRI instead of MboI, thus, allowing in vivo recombination to reconstruct the functional oncogene. Recently, this technique has been used to generate biological activity, for the human nerve growth factor receptor, by transfecting DNA defining part of this gene with DNA sequences that were selected from a normal human lambda library that hybridize to the partial gene encoding this receptor (24). The resulting transfectants expressed a new growth factor receptor that exhibited NGF binding activity (24). This approach may be useful if the above approaches are negative in the isolation of gene(s) responsible for oncogenic transformation of CREF cells.

It is possible that the gene(s) responsible for oncogenic conversion of CREF-Trans 6 cells can not be isolated using genomic clones and searching for this human gene by virtue of its close association with human Alu sequences. As an alternative to the initial approach, one may base the gene isolation strategies upon isolation of cDNAs reflecting different mRNA species or IRNA levels among highly related non-oncogenic CREF cells and the tertiary transfectants of these CREF cells displaying an oncogenic phenotype. The difference between CREF cell gene expression and tumorigenic LN-CAP transfectants is likely due to the expression of genes from human prostatic carcinoma DNA. Based on this hypothesis, RNA from cloned tertiary transfectants may be used to construct cDNA/lambda-gt10 libraries and these libraries will be screened with $^{32}$p-labeled CDNA probes generated from CREF mRNA or CREF transfectant MRNA.

Ten micrograms of poly A$^+$ RNA will be sufficient to construct libraries which should contain $10^6$ independent recombinant phage. λgt 10-cDNA libraries of this size should contain sequences present at levels of less than 0.001% of the total mRNA. λgt10-cDNA libraries constructed from tertiary LN-CaP CREF cell transfectants will be screened by a number of strategies (comparative, competitive and subtractive screening (29, 10–13) to isolate cDNA clones representing mRNAs expressed uniquely or at height levels in CREF-transfectants compared to CREF cells.

To screen the libraries for genes expressed in LN-CaP-transfected CREF cells but not in CREF-Trans 6 cells, duplicate nitrocellulose filters containing the appropriate recombinant phage-tertiary CREF transfectant cDNA may be hybridized to $^{32}$P-labeled cDNA probes made from untransformed CREF-Trans 6 cells and tumor-inducing LN-CaP transfected CREF cells (10). As a second screening approach, nitrocellulose filters containing recombinant phage DNA molecules (containing cloned cDNA from CREF-Trans 6 or CREF-Trans 6 cells transfected using LN-CaP DNA) may be hybridized to $^{32}$P-labeled cDNA probes prepared from tertiary transfectant CREF cells in the presence of several hundred-fold excess of other CREF mRNA (11). As a third approach one may also use subtractive screening procedures in which nitrocellulose filters containing recombinant phage-tertiary transfectant DNA molecules are hybridized to $^{32}$P-labeled cDNA probes enriched in untransformed CREF cell sequences or tertiary CREF cell cDNAs (12,13). Using these procedures it should be possible to isolate specific recombinant phage which contain gene sequences that are uniquely expressed or over expressed in transfected CREF cells compared to CREF cells.

cDNA clones representing mRNA differentially expressed among tumorigenic and nontumorigenic cells may be assigned to homology groups by cross hybridization analysis and mapped using restriction endonucleases (29). The largest cDNA insert from each homology grouping will be used to characterize the size and abundance of homologous mRNAs, if present, from CREF-Trans 6 cells, LN-CAP cells and CREF-Trans 6 cells transfected using LN-CaP DNA to insure that the cloned cDNA represents human-specific mRNA and that it is from a gene that may be responsible for the oncogenic conversion of CREF-Trans 6 cells and the control of prostatic carcinoma. Northern blot analyses may also indicate if these genes are also expressed in: (a) normal prostate tissue, possibly in lower levels; (b) clinical tissue samples derived from prostate tumors manifesting different stages of progression of prostatic carcinoma in humans; and (c) prostatic cells from normal or cancerous tissue derived from rats.

Recombinant phage that contain cDNAs representing differentially expressed mRNAs may then be used as a probe in Northern blot analysis of mRNA extracted from CREF-Trans 6 cells in addition to mRNA from the cloned tertiary transfectants. If the Northern analyses identify genes expressed solely in the transfected cells, these cDNA clones may then be employed as a probe to identify cosmids of phage from genomic libraries of the tertiary transfectant DNA in order to isolate and identify gene sequences that control expression of these genes. Once the genomic counterparts are isolated, the structure of the oncogene(s) can be studied by the techniques of $S_1$ nuclease mapping (29), restriction endonucleases mapping (29), and by DNA sequencing (14).

To confirm the biological function of the cloned cDNA(s), the cDNA(s) may be excised from recombinant λgt10 DNA and the cDNA may be inserted into the pCD expression vector (15,16). The pCD-cDNA recombinant plasmids may then be cloned into a λ-NMT bacteriophage which contains the neomycin gene fused to an SV40 early gene transcription unit, thus conferring G418 resistance to mammalian cell transfectants and a strong promotor for cDNA expression (15). λNMT-pCD-cDNA recombinant bacteriophage particles may be used directly for high efficiency transfection of CREF cells. The G418-resistant population may be tested for tumorigenicity in nude mice and transformation-associated traits such as changes in cell morphology, growth and the ability to grow in agar-containing medium.

Identification of a gene(s) regulating the tumor-inducing phenotype in CREF cells from human prostatic carcinoma cells will be valuable in: (a) determining if a similar gene(s) is present and expressed in other human prostatic carcinoma cell lines, including DU-145 and PC-3; (b) determining if a similar gene(s) is present and/or expressed in normal human prostate, benign prostatic hypertrophy and prostatic carcinoma tissue representing different stages in the evolution of this disease; (c) determining of a homologous gene(s) is expressed in rat prostatic carcinoma cells and if expressed of this gene is altered in cells exhibiting different degrees of metastatic potential; (d) identifying and characterizing specific protein(s) which may be involved in mediating the tumor-inducing phenotype in CREF cells, and (e) generating defined immunological reagents which might be useful in the diagnosis of specific stages of prostate cancer and in monitoring the course of therapy in patients receiving treatment for prostatic cancer:

RESULTS AND DISCUSSION

Studies over the past several years have been based on several hypotheses. (1) Human cancer develops as a consequence of heritable alterations in a cells genotype. These heritable alterations may involve direct changes in the structure and/or expression of specific genes which regulate expression of the transformed state. Genotypic markers and potential inducers of the tumor cell phenotype include the activation of specific oncogenic elements and/or the loss or inactivation of tumor suppressor elements (45,46). (2) The neoplastic phenotype is often characterized by the surface expression of novel tumor associated antigen (TAA) subsets which are specific for different histogolgical types of tumors and which may be differentially expressed in patients with the same tumor histotype. By employing specific cytokines, the level of expression of specific TAAs can be increased resulting in the improved diagnosis, imaging and ultimately enhanced monoclonal antibody (MoAb) based therapy of cancer (47,48,49). (3) the specific TAA subset expressed in a particular tumor may not be recognized by the patients' own immune system, thereby resulting in the inability of the patient to mount an effective immunological response and destroy the neoplastic lesion. This problem can be overcome by the exogenous application of MoAbs (specifically human MoAbs; primate MoAbs or chimerized murine MoAbs), augmenting the patients' immune potential with cytokines and expression vector-based immunopotentiators and/or modifying a patients' own tumor cells to function as a vaccine. (4) In many cases, the genetic elements(s) which induces the tumorigenic phenotype may also encode for the specific cell surface TAA. It should, therefore, be possible to cotransfer both the tumorigenic phenotype and its corresponding TAA subset to suitable recipient cells by DNA-transfer techniques.

Studies to directly test many of the above hypotheses have been conducted over the past several years and a number of assumptions have now been validated. One initial test case has involved studies on the genetic and immunologic basis of human prostate carcinoma development. Prostate cancer is currently the most common cancer in adult males and the leading cause of cancer deaths in males over the age of 55. With a prolongation of life span in humans, the incidence of prostatic carcinoma development and acquisition of metastatic potential by prostatic carcinoma cells (specifically to bone) has not been resolved. Attempts to demonstrate consistent changes in the expression of known oncogenes or specific cytogenetic changes (indicative of tumor suppressor gene loss) in prostatic carcinoma cells has also not been informative. Similarly, although MoAbs are available which can identify prostatic carcinoma cells, such as prostate-specific antigen and prostate-specific acid phosphatase, these reagents are more useful in identifying cells of prostatic origin (including normal prostate, benign prostatic hypertrophy and prostatic carcinoma) as opposed to prognostic and therapeutic applications.

A procedure which has proven successful in identifying dominant acting oncogenes associated with various human malignancies has been DNA transfection. This approach was initially based on the ability of transforming oncogenes to induce morphological transformation (focus formation) in established cell lines, such as NIH-3T3. A refinement of this technique which has permitted the identification of additional oncogenes in human tumors has involved cotransfection of established cell lines with tumor DNA and a selectable antibiotic resistance gene, selection of antibiotic resistance and injection of resistant colonies into nude mice. Tumors which have developed in nude mice have been shown to contain human repetitive DNA (Alu) sequences and these tumor-derived cell lines have proven to be valuable substrates for the identification and cloning of human tumor associated oncogenes. Employing monolayer transfection techniques with NIH 3T3 cells, one of eight prostatic adenocarcinoma DNA samples and none of six benign prostatic hyperplasia samples induced transformed foci. In the one positive DNA sample, the transforming event was shown to be associated with an activated Ki-ras oncogene. These results suggest that the activation of oncogeneses in human prostatic carcinomas, at least those detected by DNA-transfection assays in NIH 3T3 cells, is not a frequent event in prostate cancer. However, by employing DNA cotransfection techniques followed by tumor induction in nude mice using a specific subclone of the cloned rat embryo fibroblast cell line (CREF) (33) developed in our laboratory (CREF-Trans 6) we have now successfully transferred the gene(s) which may mediate or is correlated with prostatic carcinoma development in humans. Employing the same approach in CREF-Trans 6 cells with DNA from normal tissue or salmon sperm DNA has not resulted in either morphological transformation in vitro or tumor development in nude mice. Similarly, prostatic carcinoma DNA capable of tumorigenic conversion in CREF-Trans 6 cells has not induced malignant conversion or morphological transformation in NIH 3T3 cells These observations indicate that the CREF-Trans 6/transfection system may be amenable for the identification of a putative tumor-inducing, but not a focus-inducing, oncogene(s) which may be involved in the development of prostatic carcinoma in humans.

CREF cells cotransfected with DNA from the human prostatic carcinoma cell line, LNCaP, and pSV2neo induce tumors in nude mice. Both 1° (first transfection) and 2° (second transfection) tumor-derived CREF cells contain human Alu sequences. All of the tumors contain apparently unique Alu fragments in addition to a common Alu fragment of approximately 7.5 kb (FIG. 1). This observation suggests that the putative tumor-inducing gene derived from these human prostate carcinoma cells is located adjacent to this DNA sequence. Employing 1° and 2° tumors derived from nude mice injected with CREF cells transfected with human prostate DNA, various strategies can now be used to isolate the gene mediating the tumor cell phenotype. One approach would be to prepare genomic DNA libraries in EMBL3 phage using the DNA corresponding to Alu positive signals found in 1° and 2° tumor-derived CREF transfectants. Alu positive clones can then be identified, subcloned and the presence of exons can be determined by Northern blotting. Subclones hybridizing to similar size RNAs on Northern blots can be further characterized by sequencing and they can be used as a probe for screening either genomic or cDNA LNCaP libraries. A second approach would be to use Alu specific probes to identify and amplify DNA adjacent to these sequences in 1° and 2° tumor-derived CREF-Trans 6 transfectants by the polymerase chain reaction (PCR). These amplified DNA sequences can then be cloned directly into expression vector systems and tested for tumor-inducing potential in nude mice. A third approach would be to make subtracted libraries from CREF NMT 4 and CREF-Trans 6 cells. Additional approaches could be employed for identifying and cloning the gene in LNCaP cells which mediates tumor formation in CREF cells and which may be involved in prostatic carcinoma development in humans. These include: (l) Partially digesting LNCaP DNA with SauIIIAI, selecting DNAs of 30 to 35 kb and producing a genomic library in a genomic neo-expression vector system. These DNAs can then be transfected into CREF cells and neo-resistance and injecting pooled cell populations into nude mice for tumor formation. The likelihood of successfully identifying and cloning the putative tumor-inducing gene derived from LNCaP cells using the above strategies is high. In addition, the approaches outlined above can also be used to identify and clone other rumor-inducing genes from other specific human malignancies which have been transfected and expressed in CREF-Trans 6 cells. Once identified, the putative tumor-inducing gene from LNCaP (and other identified, the putative tumor-inducing gene from LNCaP (and other tumors) can then be used as a probe to determine its organization and expression in normal prostate, benign prostatic hypertrophy and different Gleason stage prostatic carcinomas in humans. The potential role of this tumor-inducing gene from LNCap cells in mediating metastasis in prostatic carcinoma cells could also be addressed.

As indicated above, the neoplastic phenotype is often characterized by the surface expression of novel tumor associated antigen (TAA) subsets which are specific for different histological types of tumors. It is possible that in certain cases, the genetic element(s) which induce the tumorigenic phenotype may also encode these specific cell surface TAAs. In a number of cases, TAAs have proven to be suitable targets for MoAb-based therapy resulting in direct tumor growth suppression. We have directly tested the possible relationship between induction of the tumor cell phenotype and expression of specific TAAs using LNCaP transfected-tumor-derived CREF-Trans 6 cells (CREF 4 NMT).

Figure 2:
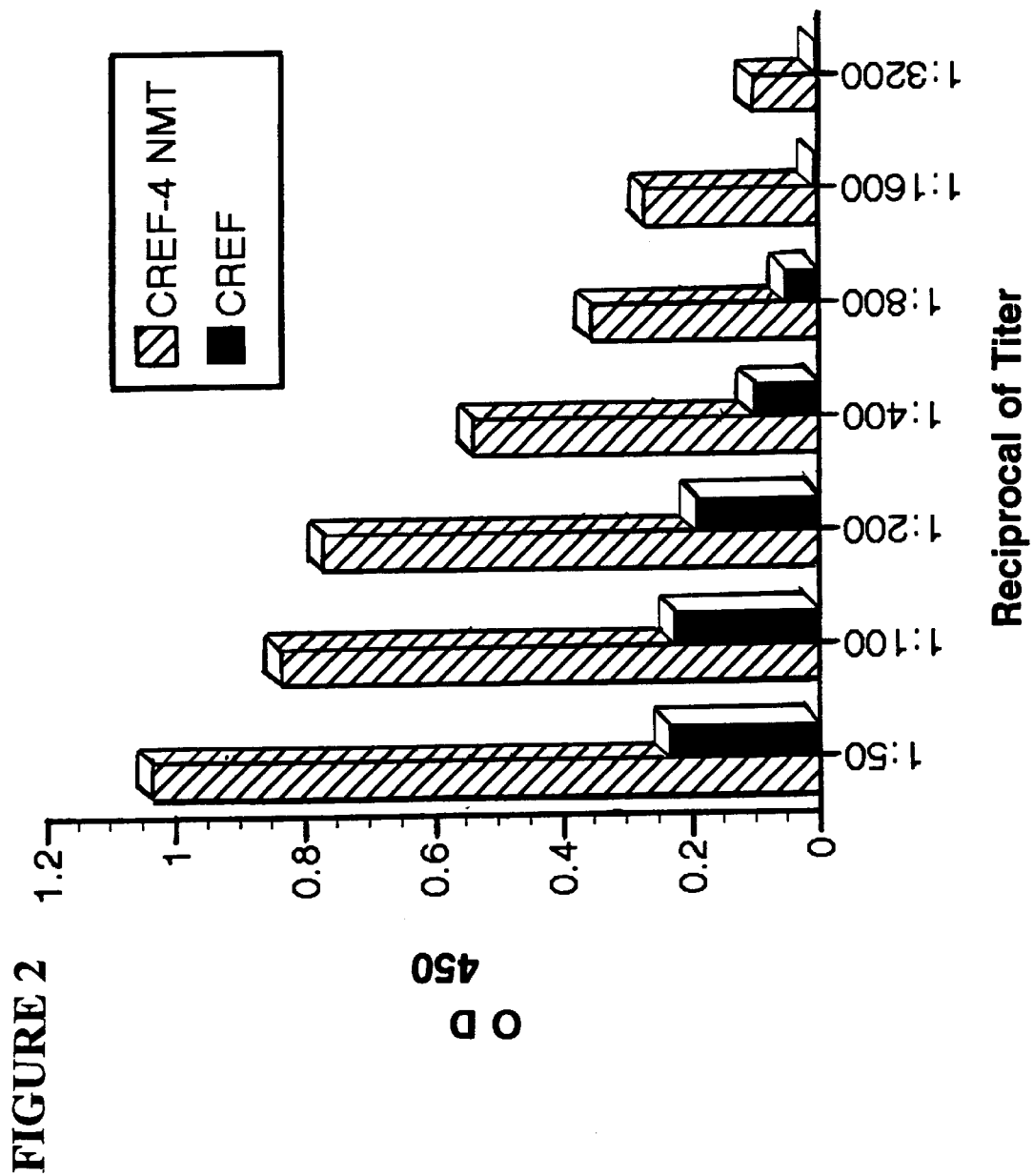
FIG. 2. Titration of CREF 4 NMT-coated and CREF-Trans 6 (represented as CREF in FIG. 2) -coated antisera against LNCaP. Animals immunized with nude mouse tumor-derived CREF-Trans 6 cells transfected with LNCaP DNA (CREF-4 NMT) exhibit an immune response to the original LNCaP cells. CREF-Trans 6 cells lacking the putative human TAAs from LNCaP cells do not generate an immune response to LNCaP cells.
Figure 3:
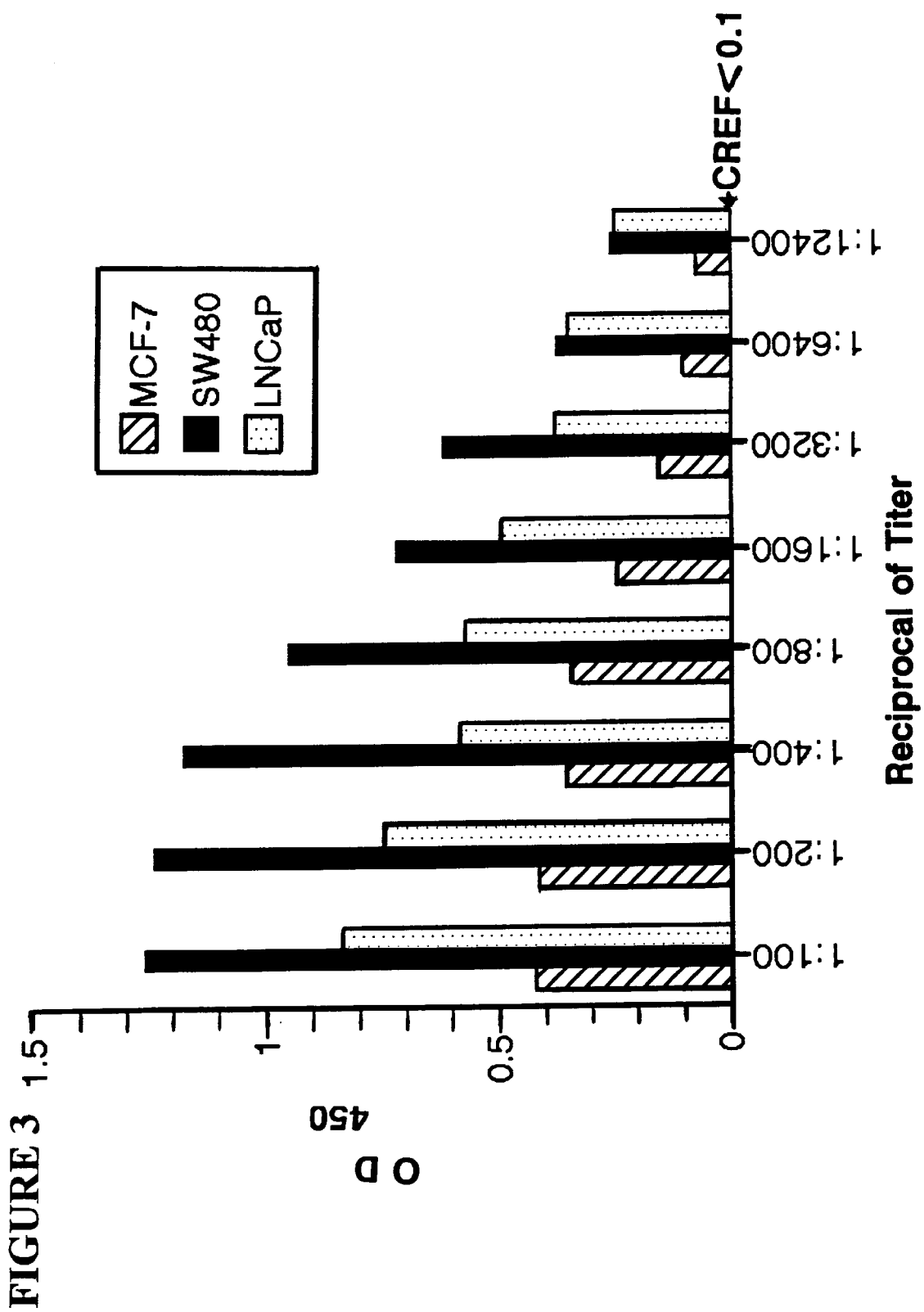
FIG. 3. Binding of CREF-4 NMT polyclonal antisera to human carcinoma cells. Polyclonal antibody generated against high titer CREF-Trans 6 cells (represented as CREF cells in FIG. 3) transfected with LNCaP DNA (CREF-4 NMT) bind to human prostatic, breast and colorectal carcinoma cell lines. In contrast, polyclonal antibody generated against CREF-Trans 6 cells coated with the same high titer CREF-Trans 6 antisera as CREF-4 NMT does not bind to human carcinoma derived cell lines.
Figure 4:
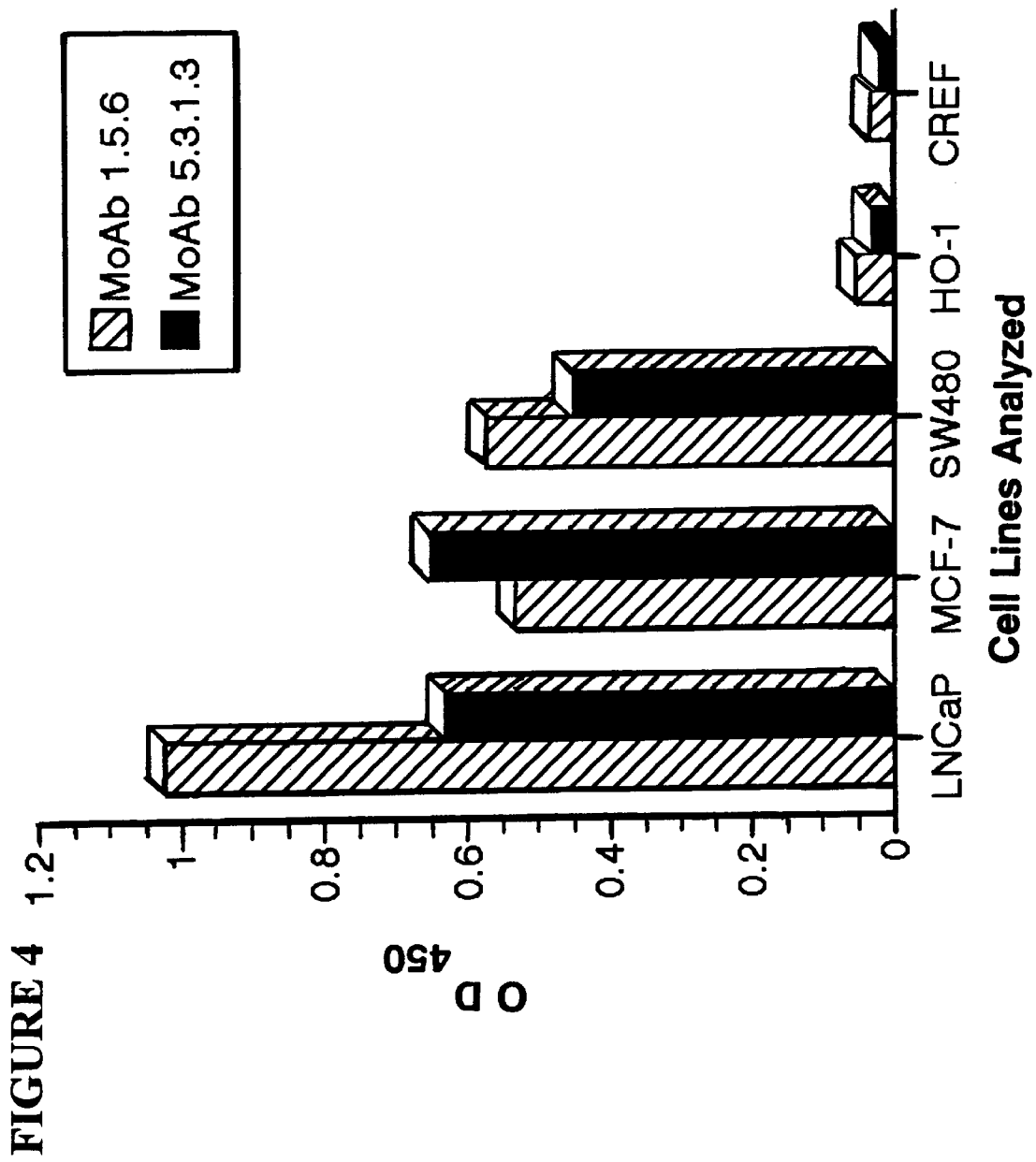
FIG. 4. Binding of CREF-4 NMT MoAbs to human tumor cell lines and CREF-Trans 6. MoAbs developed from animals immunized with high-titer CREF-Trans 6 antisera treated CREF-4 NMT cells display good specificity for LNCaP and other human carcinomas. In contrast, the same MoAbs do not bind to HO-I human melanoma, WI-38 human skin fibroblast or CREF-Trans 6 cells (represented as CREF in FIG. 4).

By injecting mice with CREF 4 NMT cells coated with a high specific activity polyclonal antibody generated against CREF-Trans 6 cells, we have successfully generated both polyclonal and MoAbs interacting with antigens expressed on CREF 4 NMT and LNCaP cells (Table 1 and FIGS. 2, 3 and 4). CREF-Trans 6 cells generated an immune response to CREF-Trans 6 and CREF 4 NMT cells, but not to cells of human origin. In contrast, CREF-Trans 6 coated CREF 4 NMT cells generated a polyclonal antibody response which identified

TABLE 1

| CELL LINE | ORIGIN | MOUSE ANTISERA GENERATED AGAINST | |
|---|---|---|---|
| | | CREF | CREF-NMT |
| CREF-Trans 6 | Rat embryo Fibroblast | + | − |
| CREF-NMT 4 | LNCaP-Transfected Tumor-Derived CREF | + | + |
| LNCaP | Human Prostatic Carcinoma | − | + |
| SW480 | Human Colo-Rectal Carcinoma | − | + |
| MCF-7 | Human Breast Carcinoma | − | + |
| Colo38 | Human Melanoma | − | − | antigens on CREF 4 NMT, LNCaP, human colo-rectal carcinoma (SW480) and human breast carcinoma (MCF-7),
but not on CREF-Trans 6, human skin fibroblasts (WI-38) or human melanoma (HO-1) cells (Table 4 and FIG. 2). Further characterization, by titration analysis, of the polyclonal antibody produced by injecting mice with CREF-Trans 6 coated CREF 4 NMT cells is shown in FIG. 3. As can be seen, the anti-CREF 4 NMT polyclonal antibody was able to bind to human prostatic, breast and colo-rectal carcinoma cell lines. MoAbs were then generated by standard procedures from animals hyperimmunized with high-titer CREF antisera coated CREF 4 NMT cells. As shown in FIG. 4, these MoAbs (MoAb 1.5.6 and MoAb 5.3.1.3) have good reactivity with LNCaP as well as other human carcinomas. In contrast, these MoAbs do not bind to HO-1, WI-38 or CREF cells. These results clearly indicate that the gene(s) which have been transferred to CREF-Trans 6 cells from LNCaP DNA are being expressed in transfected cells and they can be used to generate MoAbs which react with the original cells from which human tumor DNA was isolated.

Figure 5:
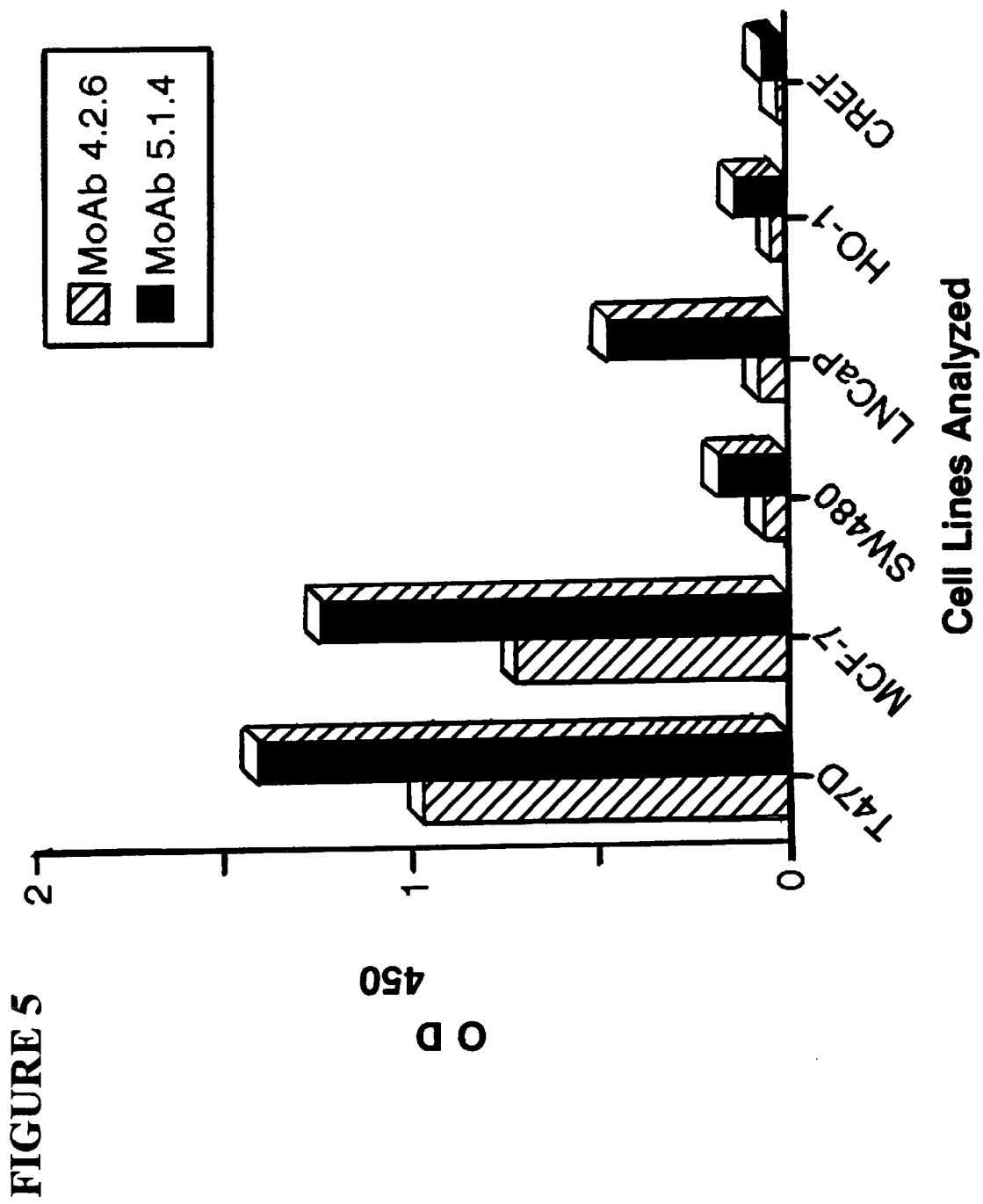
FIG. 5. Binding of CREF-T47D MoAbs to human cell lines and CREF-Trans 6 cells. MoAbs generated against nude mouse tumor-derived DNA-transfected CREF-Trans 6 cells exhibit good specificity for human breast carcinoma cells. MoAb 5.1.4 also displays some binding to human prostatic carcinoma cells. MoAbs do not bind to HO-I human melanoma cells or nontransfected CREF-Trans 6 cells (represented as CREF in FIG. 5).
Figure 6:
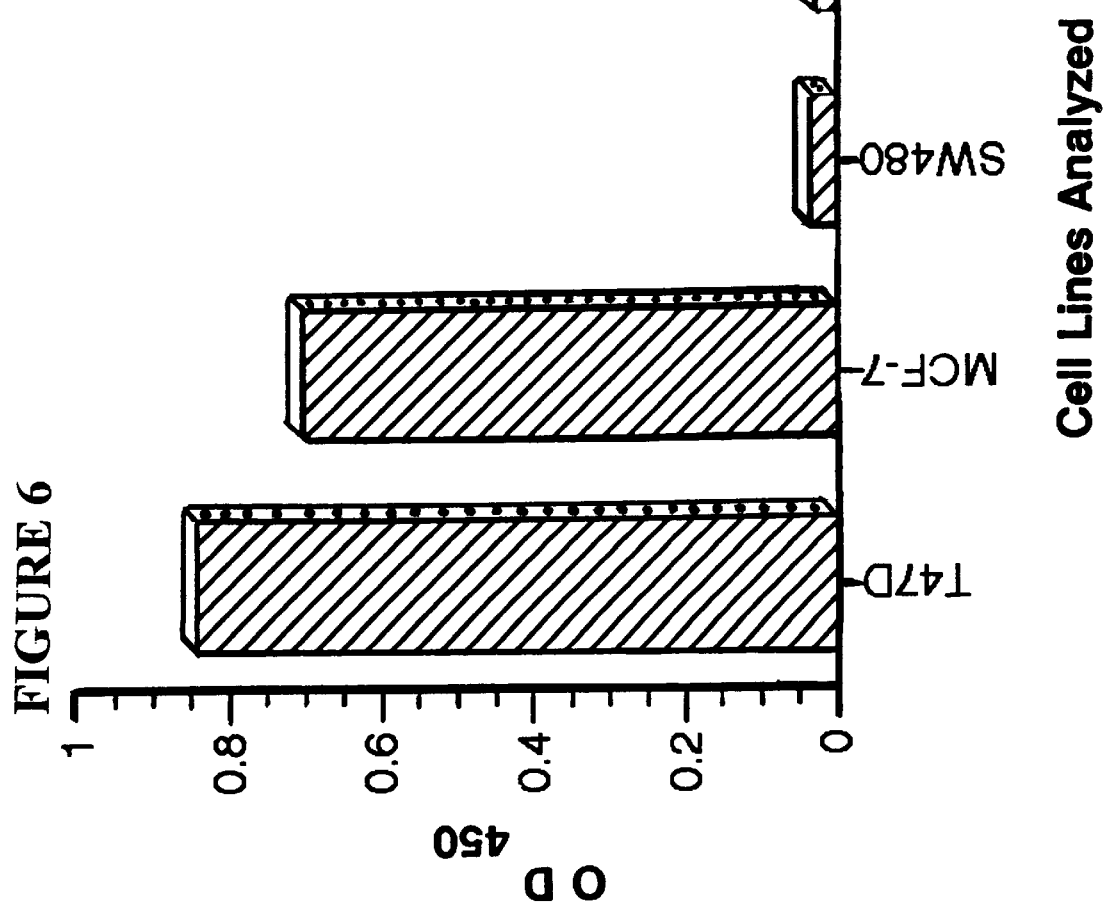
FIG. 6. Binding of MoAb 5.1.4 (CREF-T47D) ascites to human and CREF-Trans 6 cell lines (represented as CREF in FIG. 6). MoAb 5.1.4 developed against animals immunized with nude mouse tumor-derived CREF-Trans 6 cells transfected with human breast carcinoma DNA from T47D cells (which had been coated prior to injection in animals with high-titer CREF-Trans 6 antisera) continue to display good specificity for human breast carcinoma cells following subcloning and ascites formation.

The CREF-Trans 6 system has now been tested for the expression of tumor-inducing gene(s) from other human tumor cell lines as well as primary human tumor DNA samples. We have successfully transferred a tumorigenic phenotype from a human breast carcinoma cell line (T47D), a human glioblastoma multiform (stage IV astrocytoma) cell line (GBM-18) and primary human glioblastoma multiform (stage IV astrocytoma) DNA from a primary tumor. In the case of CREF-T47D transfectants we have been able to detect Alu sequences which, as expected, are different in size than those found in CREF 4 NMT cells. In addition, by using our antibody-coating technique with high specific activity CREF antisera, we have been able to generate a MoAb (4.2.6) which binds to T47D as well as MCF-7 cells, but not to SW480, LNCaP, HO-1 or CREF cells (FIG. 5). A second MoAb (5.1.4) generated following exposure of animals to CREF-Trans 6 antisera coated CREF-T47D cells, not only binds to T47D and MCF-7, but it also reacts with LNCaP cells. These results suggest that the epitope recognized by MoAb 5.1.4 is expressed in breast and prostatic carcinoma cells, but not to the same degree in SW480 or HO-1 cells. Further studies of MoAbs 5.1.4, indicate that this MoAb retains good specificity for human breast carcinoma cells following subcloning and ascites formation (FIG. 6). A further analysis of these MoAbs (as well as MoAbs 1.5.6 and 5.3.1.3 generated against CREF 4 NMT cells) with a larger number of cell types, as well an analysis of sectioned tumor tissue, will determine the specificity and diagnostic utility of these MoAbs.

In summary, we have developed a general method for identifying genes and producing immunological reagents which encode TAA of human origin. An association between the tumor-inducing gene transferred by transfection into CREF cells and human encoded gene products (TAAs) was suggested by the ability to generate both polyclonal and MoAbs which bind to human prostatic carcinoma cells. In addition, by using the CREF/Transfection/Monoclonal Antibody technology we have also succeeded in transferring gene(s) which may mediate or are associated with human breast carcinoma and glioblastoma multiform and developing both polyclonal and MoAbs recognizing antigens expressed in human breast carcinomas and other carcinomas. The CREF/Transfection/Monoclonal Antibody technology has also been used to identity defined transfected and expressed surface molecules, including the cloned human 170,000 molecular weight (P-glycoprotein) multi-drug resistance gene. CREF and human tumor (breast carcinoma and glioblastoma) cells were transfected with the cloned mdr-1 gene, selected for colchicine resistance and the presence and expression of the mdr-1 gene was demonstrated by Southern and Northern analysis, respectively. These transfected CREF cells were then used to generate MoAbs which react with the P-glycoprotein expressed in transfected human breast and. glioblastoma cells expressing an MDR phenotype.

REFERENCES

1. Fasano O, Birnbaum D, Edlund L, Fogh J and Wigler M: Mol Cell Biol. 1985.
2. Liaw W S, Ng A K, Liu Z, Duigou G J, Zimmer S G and Fisher P B: Amer Urol Assocl, Abstract, in press, 1987.
3. Babiss L E, Young C S H, Fisher P B and Ginsberg H S: J Virol 46:454, 1983.
4. Weinberg R A: Science 230:770, 1985.
5. Bishop J M: Ann Rev Riochem 52:301, 1983.
6. Bishop J M: Cell 42:23, 1985.
7. Der C J, Krontiris T G and Cooper G M: Proc Natl Acad Sci USA 79:3637, 1982.
8. Goldfarb N, Shimizu K, Perucho N and Wigler M: Nature 296:404, 1982.
9. Parada L, Tabin C, Shih C and Weinberg R: Nature 297:474, 1982.
10. Santos E, Trowick S R, Aaronson S A, Puciani S and Barbacid M: Nature 298:343, 1982.
11. Cooper, C S, Park, M, Blair, D G, Tainsky, M A, Huebner, K, Croce, C M and Vande Woude: Nature 311:29, 1984.
12. Brown B, Brady G, Mattern J and Shutz G: Carcenogenesis, 5:1323, 1984.
13. Young D, Waitches G, Birchmeier C, Fasano O and Wigler M: Cell 45:711, 1986.
14. Fisher P B, Babiss L E, Weinstein I B and Ginsberg H S: Proc Natl Acad Sci USA, 79:3527, 1982.
15. Ashburner N and Ronner J J: Cell 17:241, 1979.
16. Levinson W, Oppermann H and Jackson J: Biochem Beiophys Acta 606:170, 1980.
17. Anathan J, Goldberg A L and Voellmy R: Science 232:522, 1986.
18. Buttyan R, Zakeri Z and Wolgemuth D J: The Gerontologist 26:73A, 1986.
19. Fidler I J and Hart I R: Science 217:998, 1982.
20. Poste G and Greig R: Invasion and Metatstasis 2:137, 1982.
21. Heppner G H: Cancer Res 44:2259, 1984.
22. Rabiss L E, Fisher P B and Ginsberg H S: J Viorl 49:731, 1984.
23. Jelinek, W R, Toomey T P, Leinwand L, Duncan C H, Biro P A, Choudary P V, Weissman S M and Schmid C W: Proc Natl Acad Sci USQ 77:1398, 1980.
24. Chao M V, Bothwell M A, Ross A H, Koprowski H. Lananhan A A, Buck C R and Sehgal A; Science 232:518, 1986.
25. Kaiser K and Murray N: in *DNA Cloning: A Practical Approach=1*, vol 1, Glover D M (Ed), 1985.
26. Benton W D and Davis R W: Science 196:180, 1977.
27. Favalaro J, Freisman R and Kamen R: Methods Enzymol 65:718, 1980.
28. Maniatis T, Fritsch E F and Sambrook J: *Molecular Cloning: A Laboratory Manual*, Cold Spring Harbor Laboratory.
29. St John T P and Davis R W: Cell 16:443, 1979.
30. Mangiarotti G, Chung S, Zuker C and Lodish H F: Nucleic Acids Res 9:947, 1981.
31. Zuker C and Lodish H F: Proc Natl Acad Sci USA 78:5386, 1981.
32. Scott M R D, Westphal K H and Rigby, P W J: Cell 34:557, 1983.
33. Maxim A M and Gilbert W: Proc Natl Acad Sci USA 34:360, 1977.
34. Okayama H and Berg P: Mol Cell Biol 5:1136, 1985.
35. Mulligan R C and Berg P L Proc Natl Acad Sci USA 78:2972, 1981.
36. Liaw W S, Duigou G J, Ng A K and Fisher P B: unpublished data, 1987
37. Dorsch-Hasler K, Fisher P B, Weinstein I B and Ginsberg H S: J. Virol 34:385, 1980.
38. Greiner J W, Schlom J, Pestka S, Langer J A, Giacomini P, Kusama M, Ferrone S and Fisher P B: Pharmacol Therapeut, in press, 1987.
39. Drebin J A, Stern D F, Link V C, Weinberg R A and Green M I: Nature 312:545, 1985.
40. Roth J A, Scuderi P, Westin E and Gallo R C: Surgery 96:264, 1984.
41. Roth J A, Ames R S, Restrepo C and Scuderi P: J Immunol 137:2385, 1986.
42. Hollingsworth N A, Rebellato L N, Moore J W, Finn O J and Metzgar R S: Cancer Res. 46:2482, 1986.
43. Brickell P M, Latchman D S, Murphy D, Willison K and Rigby P W J: Nature 306:756, 1983.
44. Carpenter C D, Brushin A M, Hardin P E, Keast M J, Anstrom J, Tyner A L, Brandhorst B P and Klein W H: Cell 36:663, 1984.
45. Babiss L E, Zimmer 56, and Fisher P B: Science 228:1099, 1985.
46. Duigou G J, Babiss L E, Iman D S, Shay J W, Fisher P G: Molecular and Cellular Biology 10:2027, 1990.
47. Greiner J W, Guadagni F, Noguchi P, Pestka S, Colcher O, Fisher P B, Schlom J: Science 235:895, 1987.
48. Leon J A, Mesa-Tejada R, Gutierrez M C, Estabrook A, Greiner J W, Schlom J, Fisher P B: Anticancer Research 9:1639, 1989.
49. Guarini L, Temponi M, Bruce J N, Bollon A P, Duigou G J, Moulton T A, Ferrone S, Fisher P B: Int'l J. of Cancer, in press, 1990.
50. Schlom J, Colcher D, Horan Hand P, Greiner J, Wunderlich D, Weeks N, Fisher P B, Noguchi P, Pestka S and Kufe D: In: Klein G, Weinhouse S and Light S (Eds), *Advances in Cance Research*, Academic Press, New York, Vol 43:143, 1985.
51. Reisfeld R A and Ferrone S (Eds): *Melanoma Antiaens and Antibodies*, Plenum Press, New York, 1982.
52. Liu Z, Spooner R J R, Fisher P B and Ng A K: Unpublished data, 1986.
53. Liu Z, Borek C and Ng A K: Unpublished data, 1987.
54. Kohler G and Milstein C: Nature 256:495, 1975.
55. Nussenzweig M C, Steinman R N, Witmer M D and Gutchinov G: Proc Natl Acad Sci USA, 79:161, 1982.
56. Ng A K, Pelligrino M A, Imai K and Ferrone S: J Immunol 127:443, 1981.
57. Giacomini P, Aguzzi A, Pestka S, Fisher P B and Ferrone S: J Immunol 188:1649, 1984.

58. O'Farrell J: J Biol Chem 250:4007, 1975.
59. Garrels J I: J Biol Chem 254:7951, 1979.

What is claimed is:

1. A method for preparing a hybridoma cell line which produces a monoclonal antibody which specifically recognizes and binds to a tumor associated antigen which comprises:

a) cotransfecting a CREF-Trans 6 cell line (ATCC Accession No. CRL 10584) with DNA isolated from a neoplastic, human cell and a plasmid which encodes a selectable or identifiable trait;
   b) selecting transfected cells which express the selectable or identifiable trait;
   c) recovering the cells selected in step (b);
   d) injecting the cells so recovered in step (c) into a suitable first murine host;
   e) maintaining the resulting first murine host for a period of time effective to induce the cells injected in step (d) to form a tumor in the first murine host;
   f) isolating the tumor formed in step (e);
   g) obtaining tumor cells from the isolated tumor in step (f);
   h) coating the tumor cells obtained in step (g) with an antiserum generated against the CREE Trans-6 cell line;
   i) injecting the antiserum-coated cells from step (h) into a plurality of suitable second murine hosts;
   j) screening the resulting second hosts from step (i) to identify hosts which produce serum reactive with the neoplastic, human cell;
   k) removing spleens from the second hosts so identified in step (j);
   l) preparing from the spleens so removed in step (k) hybridomas; and
   m) recovering therefrom a hybridoma cell line which produces a monoclonal antibody which specifically recognizes and binds to the tumor associated antigen.

2. A method of claim 1, wherein the neoplastic, human cell is a metatastic tumor cell.

3. A method of claim 1, wherein the neoplastic human cell is a human prostatic carcinoma cell.

4. A method of producing a monoclonal antibody which specifically recognizes and binds to a cell surface antigen associated with a neoplastic, human cell which comprises:

(a) producing a hybridoma according to the method of claim 1; and
   (b) recovering from the hybridoma so produced the monoclonal antibody.

* * * * *